US009359421B2

(12) United States Patent
Ivanov et al.

(10) Patent No.: US 9,359,421 B2
(45) Date of Patent: Jun. 7, 2016

(54) SUPPRESSOR OF THE ENDOGENOUS INTERFERON-GAMMA

(71) Applicant: TIGO GmbH, Wiesbaden (DE)

(72) Inventors: Ivan Ivanov, Sofia (BG); Genoveva Nacheva, Sofia (BG); Stefan Petrov, Sofia (BG); Hans-Guenther Grigoleit, Wiesbaden (DE)

(73) Assignee: TIGO GmbH, Wiesbaden (DE)

( * ) Notice: Subject to any disclaimer, the term of this patent is extended or adjusted under 35 U.S.C. 154(b) by 0 days.

(21) Appl. No.: 14/243,861

(22) Filed: Apr. 2, 2014

(65) Prior Publication Data

US 2014/0212383 A1 Jul. 31, 2014

Related U.S. Application Data

(63) Continuation-in-part of application No. 12/735,882, filed as application No. PCT/BG2008/000025 on Dec. 2, 2008, now abandoned.

(30) Foreign Application Priority Data

Apr. 8, 2008 (BG) ........................................ 110103

(51) Int. Cl.
*C07K 14/57* (2006.01)
*A61K 38/21* (2006.01)
*A61K 38/00* (2006.01)

(52) U.S. Cl.
CPC ............... *C07K 14/57* (2013.01); *A61K 38/217* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 4,832,959 | A | 5/1989 | Engels et al. | |
| 6,958,388 | B2 * | 10/2005 | Van Den Hazel et al. | 530/351 |
| 2003/0082138 | A1 | 5/2003 | Masuoka | |

FOREIGN PATENT DOCUMENTS

| | | | |
|---|---|---|---|
| AT | 393690 | | 11/1991 |
| CA | 2299361 | | 2/1999 |
| CA | 2361081 | | 9/2010 |
| EP | 0446582 | | 1/1991 |
| RU | 2073522 | | 2/1997 |
| RU | 2166959 | | 5/2001 |
| RU | 2268749 | C2 | 1/2006 |
| WO | WO 2006/009701 | A1 | 9/2006 |
| WO | WO 2006/120580 | A2 | 11/2006 |

OTHER PUBLICATIONS

Well (1990), Biochemistry, vol. 29, No. 37, pp. 8509-8517.*
Ngo et al. (1994), The protein Folding and Tertiary Structure Prediction, pp. 492-495.*
Petrov, S et al., Human interferon gamma: significance of lysine 88 for its biological activity, FEBS Journal, vol. 273, No. Suppl. 1, Jun. 2006, pp. 92-93, XP9150853, & 31st Congress of The Federation of European Biochemical Societies (FEBS); Istanbul, Turkey; Jun. 24-29, 2006.
Nacheva G et al., Human interferon gamma: Significance of the C-terminal flexible domain for its biological activity, Archives of Biochemistry and Biophysics, Academic Press, US, vol. 413, No. 1, May 1, 2003, pp. 91-98, XP002373770, ISSN: 0003-9861, DOI:10.1016/50003-9861(03)00113-9.
Ivanova E et al., Human interferon-gamma derivates to be used as potential drugs for treatment of multiple sclerosis, FEBS Journal, vol. 275, No. Suppl. 1, Jun. 2008, p. 452, XP9150854, Joint Conference of the 33rd FEBS Congress/11th IUBMB Conference;Athens, Greece; Jun. 28-Jul. 3, 2008.
International Search Report, PCT/BG 2008/000025; Mar. 19, 2009.
Supplementary European Search Report. EP2274326 B1; Jul. 29, 2011.
Johnson, "Treatment of multiple sclerosis with various interferons: The cons." Neurology, vol. 38, suppl. 2, 1988, pp. 62-64.
Martino et al. "Interferon-γ induces T lymphocyte proliferation in multiple sclerosis via a Ca2+-dependent mechanism." Journal of Neuroimmunology, vol. 62, 1995, pp. 169-176.
Vartanian et al. "Interferon-γ-induced oligodendrocyte cell death: Implications for the pathogenesis of multiple sclerosis." Molecular Medicine, vol. 1, No. 7, Nov. 1995, pp. 732-743.
Tellides et al. "Interferon-γ axis in graft arteriosclerosis." Circular Research, vol. 100, 2007, pp. 622-632.
Panitch et al. "Treatment of multiple sclerosis with gamma interferon: Exacerbations associated with the activation of the immune system." Neurology, vol. 37, 1987, pp. 1097-1102.

* cited by examiner

*Primary Examiner* — Christine J Saoud
*Assistant Examiner* — Jegatheesan Seharaseyon
(74) *Attorney, Agent, or Firm* — Polsinelli PC

(57) ABSTRACT

The invention relates to suppressors of endogenous human interferon-gamma (INF-γ) applicable in treatment of diseases associated with impaired activity of endogenous IFN-γ. The suppressors of the invention are useful in treating autoimmune diseases and for prevention of graft arteriosclerosis and rejection of organs in allograft transplanted patients. The invention includes inactive analogues or variants of IFN-γ having preserved affinity to the IFN-γ receptor, genetically modified in the domain responsible for triggering the signal transduction pathway.

10 Claims, No Drawings

SEQUENCE LISTING

```
<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: NUCLEIC ACID PRIMER

<400> SEQUENCE: 1
cccaagctta tgcaggacc                                                19

<210> SEQ ID NO 2
<211> LENGTH: 40
<212> TYPE: DNA
<213> ORGANISM: Artificial Sequence
<220> FEATURE:
<223> OTHER INFORMATION: NUCLEIC ACID PRIMER
<220> FEATURE:
<221> NAME/KEY: misc_feature
<222> LOCATION: (20)..(28)
<223> OTHER INFORMATION: n is a, c, g, or t

<400> SEQUENCE: 2
gcttttcgaa gtcatcacgn nnnnnnnngt tgctattgaa                          40

<210> SEQ ID NO 3
<211> LENGTH: 32
<212> TYPE: DNA
<213> ORGANISM: Artificial Sequence
<220> FEATURE:
<223> OTHER INFORMATION: NUCLECI ACID PRIMER

<400> SEQUENCE: 3
gcttttcgaa gtcatcacgt tgcttttgt tg                                  32

<210> SEQ ID NO 4
<211> LENGTH: 27
<212> TYPE: DNA
<213> ORGANISM: Artificial Sequence
<220> FEATURE:
<223> OTHER INFORMATION: NUCLEIC ACID PRIMER

<400> SEQUENCE: 4
cgcggatcct tagggcgaca gttctgc                                       27

<210> SEQ ID NO 5
<211> LENGTH: 143
<212> TYPE: PRT
<213> ORGANISM: Homo sapiens

<400> SEQUENCE: 5

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30
```

```
Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser Gln
    130                 135                 140

<210> SEQ ID NO 6
<211> LENGTH: 143
<212> TYPE: PRT
<213> ORGANISM: Homo sapiens

<400> SEQUENCE: 6

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Glu Met Pro Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser Gln
    130                 135                 140

<210> SEQ ID NO 7
<211> LENGTH: 143
<212> TYPE: PRT
<213> ORGANISM: Homo sapiens

<400> SEQUENCE: 7

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80
```

```
Phe Phe Asn Ser Asn Thr Asn Gly Arg Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Ala Ser Gln
130                 135                 140
```

<210> SEQ ID NO 8
<211> LENGTH: 122
<212> TYPE: PRT
<213> ORGANISM: Homo sapiens

<400> SEQUENCE: 8

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
50                  55                  60

Ser Ile Gln Lys Ser Val Glu Thr Ile Lys Glu Asp Met Asn Val Lys
65                  70                  75                  80

Phe Phe Asn Ser Asn Lys Lys Gln Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro
        115                 120
```

<210> SEQ ID NO 9
<211> LENGTH: 143
<212> TYPE: PRT
<213> ORGANISM: Homo sapiens

<400> SEQUENCE: 9

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
50                  55                  60

Ser Ile Gln Lys Ser Val Glu Thr Ile Lys Glu Asp Met Asn Val Lys
65                  70                  75                  80

Phe Phe Asn Ser Asn Lys Lys Gln Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Ala Ser Gln
130                 135                 140
```

SUPPRESSOR OF THE ENDOGENOUS INTERFERON-GAMMA

FIELD OF THE INVENTION

The present disclosure relates to suppressors of interferon-gamma (IFN-γ) comprising inactive variants of IFN-γ, and methods of using hIFN-γ variants to treat a disorder associated with aberrant function of hIFN-γ.

BACKGROUND OF THE INVENTION

Immune system protects organism from pathogenic microorganisms and foreign macromolecular substances. It identifies exogenous (foreign) bodies of molecular mass exceeding 5000 Da and produces specific antibodies for their neutralization. Immune response is regulated by numerous protein-factors (Gyiukines)-produced by specialized cells. In case of dysfunction (due to genetic disorders or infection diseases) the immune system misidentifies certain body proteins as exogenous products and produces specific antibodies for their neutralization. This process lies in the etiology of a great number of autoimmune diseases such as asthma, rheumatoid arthritis, infertility, alopecia areata, multiple sclerosis (MS) and other neurodegenerative pathologies leading to disability and early death of about 2% of the human population. There is substantial evidence that immune responses resulting in IFN-γ production are associated also with the development of graft arteriosclerosis (GA) in allograft transplanted patients. The chronic rejection of allografts (including heart) is preceded by a luminal stenosis of the blood vessels and is denoted as "graft arteriosclerosis". As many as 50% of heart transplant recipients develop angiographically detectable GA three to five years following transplantation. The only treatment currently available for GA is retransplantation, which is costly and not always possible because of shortage of suitable donors. In that sense, the demand of therapeutics for treatment autoimmune diseases and GA is a major priority of the experimental medicine and pharmacy.

Inflammation reaction accompanying the autoimmune process is related with a lavish infiltration of the target tissue with T-lymphocytes and macrophages. They are represented by CD4+ cells producing Th1 proinflammatory cytokines such as interleukin 12 (IL-12) and hIFN-γ. The latter activates mononuclear cells to produce destructive substances like lymphotoxins and tumor necrosis factor alpha (TNF-α). It is shown that the pathogenesis of most autoimmune diseases is related with an abnormal production of hIFN-γ [1-6].

The overproduction of hIFN-γ (as in the case of MS) is inhibited by parenteral application of hIFN-β 3 (see patents U.S. Pat. No. 082,138, WO9530435, CA2361081). In other patents (RU2073522, RU2187332, RU02166959) mixtures of the three different interferons IFN-α, IFN-β and IFN-γ are recommended. It is reported that high dosage (8,000,000 IU/day) of IFN-β provoke unfavorable effects such as: a) T-cells proliferation blockade; b) neutralization of IL-12 thus enhancing the IFN-γ effect; c) decreased CD4+ (Th1, Th2) and CD8+ (Tcl) cell content without changing the Th1/Th2 cell ratio [7; d) decreased levels of both pro- and anti-inflammatory cytokines [8], etc.

Another approach for neutralization of the overproduced hIFN-γ in autoimmune disease is based on the application of humanized anti-IFN-γ antibodies (patent application WO0145747 and [9-11]). The anti-hIFN-γ antibodies, however, deprive the organism from hIFN-γ and their long-term application worsens the patients' conditions.

An alternative way for decreasing the abnormal production of hIFN-γ in autoimmune diseases is based on the application of the so called "consensus interferons" IFN-con$_1$, IFN-con$_2$ and IFN-con$_3$, derivatives of the Type I hIFN-α, hIFN-β and hIFN-t (U.S. Pat. No. 0,086,534 and CA2299361). They show various side effects including toxicity.

Proteins with aminoacid sequence partly coinciding with that of the human IFN-γ have been applied as antiviral, anti-proliferative and immunomodulating agents (U.S. Pat. No. 4,832,959, WO02081507, AT393690). Their effects, however, can not cannot be presently assessed since the cited patents are not supported by clinical data.

In a recent patent application, published as WO20061099701, it is described a new approach for inhibition of the endogenous hIFN-γ using inactive recombinant analogues of the hIFN-γ with preserved affinity to the hIFN-γ receptor. Subject of the patent application are three different inactive variants of hIFN-γ (a truncated hIFN-γ lacking 27 C-terminal aminoacids, a fusion hIFN-γ-hIFN-α1 protein and a UV inactivated hIFN-γ) which compete with the natural (endogenous) hIFN-γ for the hIFN-γ receptor. Thus, competing with the hIFN-γ receptor, the inactive variants of IFN-γ suppress its activity. Since that effect is dose dependent, the effect of endogenous IFN-γ could be modulated by varying blood concentration of the hIFN-γ derivative proteins. This approach is applicable in the cases when the overproduction of endogenous hIFN-γ causes health problems as in the case of autoimmune diseases, including MS. Although these proteins are good competitors of hIFN-γ for its receptor, their tertiary structure is quite different in comparison with the native wild-type hIFN-γ, which in turn is a potential risk of formation of conformational antibodies. Related with this there is a need of new inactive variants of the hIFN-γ containing negligible changes in domains responsible for triggering the signal transduction pathway.

SUMMARY OF THE INVENTION

One aspect of the invention encompasses a composition comprising a suppressor of hIFN-γ. The suppressor of hIFN-γ is a variant hIFN-γ of SEQ ID NO: 5 deficient in inducing signal transduction and with preserved affinity to the hIFN-γ receptor, and comprises amino acid sequence modifications selected from the group consisting of amino acid substitutions at positions 86, 87, and 88, and an amino acid substitution at position 88 with a deletion of C-terminal amino acid residues.

A further aspect of the invention provides a method of modulating the biological activity of hIFN-γ. The method comprises suppressing the biological activity of hIFN-γ in a subject by administering to the subject a therapeutically effective amount of a composition comprising a suppressor of hIFN-γ. The suppressor of hIFN-γ is a variant hIFN-γ of SEQ ID NO: 5 deficient in inducing signal transduction and with preserved affinity to the hIFN-γ receptor, and comprises amino acid sequence modifications selected from the group consisting of amino acid substitutions at positions 86, 87, and 88, and an amino acid substitution at position 88 with a deletion of C-terminal amino acid residues.

Yet another aspect of the invention provides a method of treating a hIFN-γ-mediated disorder. The method comprises suppressing the biological activity of hIFN-γ in a subject by administering to the subject a therapeutically effective amount of a composition comprising a suppressor of hIFN-γ. The suppressor of hIFN-γ is a variant hIFN-γ of SEQ ID NO: 5 deficient in inducing signal transduction and with preserved affinity to the hIFN-γ receptor, and comprises amino acid sequence modifications selected from the group consisting of amino acid substitutions at positions 86, 87, and 88, and an amino acid substitution at position 88 with a deletion of C-terminal amino acid residues.

Other features and aspects of the invention are described in more detail herein.

DETAILED DESCRIPTION

The present invention provides suppressors of IFN-γ and compositions comprising suppressors of IFN-γ. A suppressor of the disclosure comprises an inactive variant of IFN-γ. IFN-γ is a cytokine that is critical for innate and adaptive immunity against viral and intracellular bacterial infections, and for tumor control. Cellular responses to IFN-γ during an immune response are activated through its binding to interferon gamma receptor (IFNGR) on the cell surface, and activation of the JAK-STAT signal transduction pathway through the receptor. As such, at a minimum, an IFN-γ protein comprises a receptor binding domain and a receptor activation domain.

The inventors have discovered minor modifications in receptor activation domains of IFN-γ that inactivate IFN-γ-mediated signal transduction. Importantly, the inventors also discovered that inactive IFN-γ variants of the disclosure comprising said minor modifications are capable of competing with, and suppressing the bioactivity of IFN-γ, in vivo or in vitro. Advantageously, the ability of a suppressor of the present disclosure to compete with bioactivity of IFN-γ is reversible, and provides a means for controlling the extent of inhibition of bioactive IFN-γ in vivo or in vitro in a dose-dependent manner by varying the concentration of suppressors of the present disclosure relative to active IFN-γ. As such, IFN-γ suppressors of the present disclosure may be used to modulate immune responses resulting from elevated IFN-γ activity without irreversibly sequestering wild type IFN-γ. Additionally, IFN-γ variants of the present disclosure resemble allelic variants of IFN-γ and are therefore not predicted to be immunogenic.

Accordingly, the present invention provides a composition comprising suppressors of IFN-γ and methods of using said suppressors of IFN-γ to treat a disorder resulting from elevated IFN-γ activity. Various aspects of the invention are described in further detail in the following sections.

I. IFN-γ Suppressor Compositions

One aspect of the present invention provides compositions comprising a suppressor of IFN-γ. A suppressor of the disclosure is an inactive variant of IFN-γ comprising modifications of IFN-γ receptor activation domains that inactivate IFN-γ-mediated signal transduction. An inactive variant of IFN-γ is capable of competing with and suppressing the bioactivity of a wild type form of IFN-γ in vivo or in vitro. While not wishing to be bound by theory, it is believed that minor modifications of the present disclosure do not alter the overall tertiary structure of IFN-γ, thereby preserving the affinity of inactive variants of IFN-γ to the IFN-γ receptor complex to compete with wild type IFN-γ. Additionally, preserved overall structure of inactive IFN-γ variants of the disclosure minimizes the potential risk of the formation of conformational antibodies against the suppressor IFN-γ variants. As such, a suppressor of the present disclosure is a variant of IFN-γ, inactive in signal transduction, but with preserved ability to bind a cell surface IFNGR.

(a) Inactive IFN-γ Variant

An inactive IFN-γ suppressor of the present disclosure comprises modifications of IFN-γ receptor activation domains. Modifications of IFN-γ activation domains may be amino acid substitutions, amino acid deletions, or amino acid insertions. Any modification of receptor activation domains of IFN-γ is contemplated herein, provided the modification inactivates signal transduction but preserves the ability of inactivated IFN-γ to compete with, and suppress the bioactivity of IFN-γ, in vivo or in vitro. Preferably, inactive IFN-γ variants of the present disclosure are derived from the wild type human IFN-γ (hIFN-γ). Numbering of amino acid residues used herein is from the N-terminus of the wild type hIFN-γ polypeptide of SEQ ID NO: 5.

Biologically active hIFN-γ is a homodimer of hIFN-γ polypeptides wherein each hIFN-γ polypeptide consists of a core of six α-helices and an extended unfolded sequence in the C-terminal region. The bioactive hIFN-γ dimer is formed by anti-parallel inter-locking of the two monomers. An inactive hIFN-γ variant of the present disclosure comprises at least one modified hIFN-γ polypeptide. As such, an inactive variant of hIFN-γ may comprise a dimer of one modified hIFN-γ polypeptide and one wild type hIFN-γ polypeptide. Preferably, an inactive variant of hIFN-γ comprises a dimer of two modified hIFN-γ polypeptides. When an inactive variant of hIFN-γ comprises a dimer of two modified hIFN-γ polypeptides, each hIFN-γ polypeptide of the hIFN-γ variant may comprise a different modification of hIFN-γ receptor activation domains. Preferably, when an inactive variant of hIFN-γ comprises a dimer of two modified hIFN-γ polypeptides, each hIFN-γ polypeptide of the hIFN-γ variant comprises the same modification of hIFN-γ receptor activation domains.

As used herein, the term "receptor activation domain" may be any amino acid residue or group of amino acid residues of hIFN-γ necessary for triggering a signal transduction pathway through the hIFN-γ receptor. Non-limiting examples of a receptor activation domain of hIFN-γ may comprise amino acid residue 86, amino acid residue 87, amino acid residue 88, the extended unfolded sequence in the C-terminal region of hIFN-γ, or combinations thereof.

Inactive hIFN-γ variants comprising amino acid modifications in amino acid residues 86, 87, 88, or combinations thereof, are contemplated herein. Preferably, amino acid modifications of amino acid residues 86, 87, 88, or combinations thereof are substituted. Preferably, amino acid residues 86, 87, and 88 are substituted. Even more preferably, amino acid residues 86, 87, and 88 are substituted using amino acid residues as described in Table 1.

TABLE 1

| Constructs and amino acid substitutions | | |
| --- | --- | --- |
| Construct No. | hIFNg gene: Nucleotide sequence corresponding to the amino acids at positions 86-88 | hIFNg: Amino acid residues at positions 86-88 |
| 2 | CCG TAC CTC | Pro Tyr Leu |
| 3 | CCC AAT TAT | Pro Asn Tyr |
| 4 | TGG TCC TCG | Trp Ser Ser |

TABLE 1-continued

Constructs and amino acid substitutions

| Construct No. | hIFNg gene: Nucleotide sequence corresponding to the amino acids at positions 86-88 | hIFNg: Amino acid residues at positions 86-88 |
|---|---|---|
| 5-3 | GTT AGT CGC | Val Ser Arg |
| 5-4 | CCG CTA AGC | Pro Leu Ser |
| 6 | CAC GTC TGT | His Val Cys |
| 8 | CCC TAC GTT | Pro Tyr Val |
| 9-1 | CGG TCT TCG | Arg Ser Ser |
| 9-2 | TTC TCT AGA | Phe Ser Arg |
| 10 | CCC TGT TGC | Pro Cys Cys |
| 11 | CCG TCC GTG | Pro Ser Val |
| 12 | ACC TTC TGG | Thr Phe Trp |
| 14 | CTC CCT TTC | Leu Pro Phe |
| 15 | GAC TTG CTG | Asp Leu Leu |
| 16 | GCC CAT CTT | Ala His Leu |
| 17 | ACC GTC CTC | Thr Val Leu |
| 18 | TGC TTC CCG | Cys Phe Pro |
| 19 | TCC ACT TTT | Ser Thr Phe |
| 21 | CCC TCT CCC | Pro Ser Pro |
| 22 | AGC TCC CTC | Ser Ser Leu |
| 23 | GTC TCT GGA | Val Ser Gly |
| 24 | ACT CCT ACC | Thr Pro Thr |
| 25 | TGT CAT TTC | Cys His Phe |
| 26 | TCA GTT TCC | Ser Val Ser |
| 27 | GAA ATG CCC | Glu Met Pro |
| 28 | CTC ACC CCT | Leu Thr Pro |
| 32 | CTG CCT CCG | Leu Pro Pro |
| 33 | CCC CCT ACT | Pro Pro Thr |
| 34 | TTC TCT CTG | Phe Ser Leu |
| 35 | TTT TTT CCC | Phe Phe Pro |
| 36 | CTG TGT CCC | Leu Cys Pro |
| 39-11 | CCC TCT GCT | Pro Ser Ala |
| 39-12 | GAC CTT CTT | Asp Leu Leu |
| 41 | GCT TTT TTT | Ala Phe Phe |
| 45 | CTG CTT CAC | Leu Leu His |
| 46-1 | ACC CTC CTC | Thr Leu Leu |
| 54 | TTC ACC GCC | Phe Thr Ala |
| 61 | CAT CCT CTC | His Pro Leu |
| 62 | TTT ACC AGA | Phe Thr Arg |
| 63 | CGT CTC CGT | Arg Leu Arg |

TABLE 1-continued

Constructs and amino acid substitutions

| Construct No. | hIFNg gene: Nucleotide sequence corresponding to the amino acids at positions 86-88 | hIFNg: Amino acid residues at positions 86-88 |
|---|---|---|
| 66 | CCA CTT GCT | Pro Leu Ala |
| 71 | TTC TGC CGT | Phe Cys Arg |
| 72 | CAC TCC CGC | His Ser Arg |
| 73 | CCT TAC CCC | Pro Tyr Pro |
| 74 | TCC CTG CTG | Ser Leu Leu |
| 75 = 76 | TGG TCT GCG | Trp Ser Ala |
| 76 = 75 | TGG TCT GCG | Trp Ser Ala |
| 77 | GCT ATC CCC | Ala Ile Pro |
| 81 | CGT CCT GTC | Arg Pro Val |
| 82-34 | TTC TGC CGT | Phe Cys Arg |
| 84 | CCC TTT GCC | Pro Phe Ala |
| 85 | CGA CGG AGC | Arg Arg Ser |
| 87 | CGC CCC TCC | Arg Pro Ser |
| 88 | CGC TCC TGC | Arg Ser Cys |
| 92 | CCC TTT CTT | Pro Phe Leu |
| 93 | CTG TAC CCC | Leu Tyr Pro |
| 94 | CCC GTC TTC | Pro Val Phe |
| 96 | CCT ATG TTC | Pro Met Phe |
| 97 | TCT TTT TTT | Ser Phe Phe |
| 103 | CAC GCT GCC | His Ala Ala |
| 104 | CCT TTT TCT | Pro Phe Ser |
| 105-2 | GCT ACA GCC | Ala Thr Ala |
| 106-1 | CTC TTC TCC | Leu Phe Ser |
| 106-2 | CTT GTC TCG | Leu Val Ser |
| 107 or 108 | TTC CTT GTC | Phe Leu Val |
| 109 | CCT CGC TCC | Pro Arg Ser |
| 110 | CCT CGC TCC | Pro Arg Ser |
| 111 | CCT CGC TCC | Pro Arg Ser |
| 112 | TTC TCC CGG | Phe Ser Arg |
| 113 | CTA TAC TTT | Leu Tyr Phe |
| 114-1 | CGT TCC GCG | Arg Ser Ala |
| 115 | CAG TTT CAT | Gln Phe His |
| 116 | GTA CTC CTC | Val Leu Leu |
| 117 | GTT CTG CCT | Val Leu Pro |
| 118 | GTC TCC GCT | Val Ser Ala |
| 119 | ACC CTC GTT | Thr Leu Val |
| 120 | CAA GCC GGC | Gln Ala Gly |

TABLE 1-continued

Constructs and amino acid substitutions

| Construct No. | hIFNg gene: Nucleotide sequence corresponding to the amino acids at positions 86-88 | hIFNg: Amino acid residues at positions 86-88 |
|---|---|---|
| 121 | CTC TCC GTC | Leu Ser Val |
| 123 | TCT TTA TTT | Ser Leu Phe |
| 126 | TAC GCT TTC | Tyr Ala Phe |
| 127-1 | CAC TAT CCT | His Tyr Pro |
| 129 | GCT AGT CTC | Ala Ser Leu |
| 131 | TTT CCC CTT | Phe Pro Leu |
| 133 | CCG CCC TCC | Pro Pro Ser |
| 134 | ACC AAT GGT | Thr Asn Gly |
| 135 | GTT TCC CCC | Val Ser Pro |
| 136 | TCC CCT CCC | Ser Pro Pro |
| 140 | TTT CCG TCT | Phe Pro Ser |
| 143 | TGT TCT CCC | Cys Ser Pro |
| 144 | TGC GCC CCT | Cys Ala Pro |
| 145 | TCC TTT TGT | Ser Phe Cys |
| 146 | CTT TTC GAG | Leu Phe Glu |
| 148 | TTC ACG CCC | Phe Thr Pro |
| 149-1 | CAC CAG CGC | His Gln Arg |
| 149-2 or 150-1 | CTT TCC TCG | Leu Ser Ser |
| 150-2 | TGG CTC TCT | Trp Leu Ser |
| 151 | CTC ACA GCG | Leu Thr Ala |
| 153 | TCT TTT TGC | Ser Phe Cys |
| 155 | ATT TCC GAT | Ile Ser Asp |
| 157 | TTT TAC ACT | Phe Tyr Thr |

Inactive hIFN-γ variants comprising amino acid modifications in the extended unfolded C-terminus of hIFN-γ are also contemplated herein. Preferably, inactive variants of hIFN-γ comprise deletion of part or all amino acid residues in the C-terminus of hIFN-γ. For instance, inactive variants of hIFN-γ may comprise deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acid residues within the C-terminal of hIFN-γ. Preferably, inactive variants of hIFN-γ comprise a deletion of 21 C-terminal amino acid residues of hIFN-γ.

Also contemplated herein are inactive hIFN-γ variants comprising amino acid modifications in amino acid residues 86, 87, 88, or combinations thereof, and amino acid modifications in the extended unfolded C-terminus of hIFN-γ. Preferably, inactive variants of hIFN-γ comprise modification of one amino acid residue selected from the group of amino acid residues 86, 87, and 88, in combination with a deletion of 21 C-terminal amino acid residues of hIFN-γ. More preferably, inactive variants of hIFN-γ comprise modification of amino acid residue 88 in combination with a deletion of 21 C-terminal amino acid residues of hIFN-γ.

An exemplary inactive variant of hIFN-γ of the present disclosure comprises substitution of amino acid residues 86, 87, and 88 with glutamic acid, methionine, and proline residues, respectively (Construct No. 27; SEQ ID NO: 6). Another exemplary inactive variant of hIFN-γ of the present disclosure comprises substitution of amino acid residues 86, 87, and 88 with threonine, asparagine, and glycine residues, respectively (Construct No. 134; SEQ ID NO: 7). Yet another exemplary inactive variant of hIFN-γ of the present disclosure comprises substitution of amino acid residue 88 with a proline residue, and deletion of 21 C-terminal amino acid residues of hIFN-γ (Construct No. Lys/Gln88/T7; SEQ ID NO: 8).

As described above, suppressors of hIFN-γ of the disclosure are inactive variants of hIFN-γ. Methods of determining in vitro and in vivo bioactivity of hIFN-γ are known in the art. Non-limiting examples of methods of determining hIFN-γ activity include measuring antiviral activity or antiproliferative activity of hIFN-γ, induction of protein kinase by hIFN-γ, oligoadenylate 2,5-A synthetase or phosphodiesterase activities, immunomodulatory assays, growth inhibition assays, and measurement of binding to cells that express interferon receptors. Preferably, antiviral activity of hIFN-γ variants is measured. Methods of measuring antiviral activity of hIFN-γ are known in the art, and may be determined by measuring the protective effect of hIFN-γ variants against the cytopathic action of the vesicular stomatitis virus (VSV) on a cell and may be as described in the examples herein and in Forti et al., 1986, Methods in Enzymology 119: 533-540, the disclosure of which is incorporated herein in its entirety. Measurement of antiproliferative activity of hIFN-γ variants is also preferred. Methods of measuring antiproliferative activity of hIFN-γ are known in the art, and may be determined using a kynurenin bioassay and may be as described in the examples herein and in Boyanova et al., 2002, Analytical Biochemistry 308: 178-181, the disclosure of which is incorporated herein in its entirety.

Inactive hIFN-γ variants may have no detectable bioactivity. Alternatively, inactive hIFN-γ variants may have reduced hIFN-γ bioactivity when compared to a wild type hIFN-γ counterpart. When inactive hIFN-γ variants have reduced bioactivity in comparison to a wild type hIFN-γ counterpart, inactive variants may have about 1, 10, 20, 30, 40, 50, 60, 70, 80, 90, 100, 110, 120, 130, 140, 150, 160, 170, 180, 190, 200, 300, 400, 500, 1000, 2000, 3000, 4000, 5000, or about 10,000 fold or more reduced activity than a wild type hIFN-γ counterpart. Preferably, when inactive hIFN-γ variants have reduced bioactivity in comparison to a wild type hIFN-γ counterpart, inactive variants have about 10, 50, 100, or about 1000 fold reduced activity compared with a wild type hIFN-γ counterpart.

When inactive hIFN-γ variants have reduced bioactivity in comparison to a wild type hIFN-γ counterpart, inactive variants may have a specific activity of about $1 \times 10^2$, $1 \times 10^3$, $1 \times 10^4$, $1 \times 10^5$, or about $1 \times 10^6$ IU/mg of the variant. Preferably, when inactive hIFN-γ variants have reduced bioactivity in comparison to a wild type hIFN-γ counterpart, inactive variants have about $1 \times 10^3$, $1 \times 10^4$, $1 \times 10^5$, or about $1 \times 10^6$ IU/mg of hIFN-γ of the variant.

As described above, IFN-γ variants are capable of competing with and suppressing the bioactivity of IFN-γ, in vivo or in vitro. Methods of determining the ability of a molecule to compete with an active molecule such as IFN-γ are known in the art and generally comprise determining the activity of the active molecule using a known method of bioactivity measurement, but in the presence of the competing molecule. For instance, hIFN-γ variants of the present disclosure may be mixed with equimolar amounts with wild type hIFN-γ, and the antiproliferative or antiviral activity of the mixtures may be determined using wild-type hIFN-γ as a standard. The results may be interpreted as follows: if the hIFN-γ variant has the same affinity to the hIFN-γ receptor as that of the wild type hIFN-γ and zero antiproliferative or antiviral activity, the activity of the equimolar mixture of both substances is 50% of that of the control (pure wild type hIFN-γ). Using this method, competition of hIFN-γ variants may be classified into high competition hIFN-γ variants, intermediate competition variants, and low competition variants. Preferably, hIFN-γ of the disclosure are high competition hIFN-γ variants.

In addition to the amino acid modifications of IFN-γ described herein, it will be appreciated by those skilled in the art that IFN-γ of the disclosure may further comprise amino acid changes other than those described above, provided the amino acid changes do not alter the functional activity of IFN-γ variants. For instance, amino acid sequence polymorphisms of IFN-γ may exist within a population (e.g., the human population). Such genetic polymorphism may exist among individuals within a population due to natural allelic variation. Such natural allelic variations may result in as much as 15% variance in the amino acid sequence of an IFN-γ of the invention. Any and all such amino acid variations and resulting polymorphisms in IFN-γ that are the result of natural allelic variation and that do not alter the functional activity of IFN-γ of the invention are intended to be within the scope of the invention. Thus, e.g., 1%, 2%, 3%, 4%, or 5% of the amino acids in IFN-γ of the invention may be replaced by another amino acid.

In addition to naturally occurring allelic variants of IFN-γ that may exist in the population, the skilled artisan will further appreciate that changes may be introduced by mutation into the amino acid sequence of IFN-γ variants of the disclosure, without altering the functional ability of the polypeptide. For instance, the polypeptides may further comprise conservatively substituted variants of the polypeptides described above. The term "conservatively substituted variant" may refer to a polypeptide wherein one or more residues have been conservatively substituted with a functionally similar residue and which displays the IFN-γ repressor activity as described herein. The phrase "conservatively substituted variant" also includes polypeptides wherein a residue is replaced with a chemically derivatized residue, provided that the resulting polypeptide displays IFN-γ repressor activity as disclosed herein.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, and between glycine and serine; the substitution of one basic residue such as lysine, arginine or histidine for another; or the substitution of one acidic residue, such as aspartic acid or glutamic acid, for another.

Polypeptides of the present invention also include peptides comprising one or more additions and/or deletions of residues relative to the sequence of a polypeptide whose sequence is disclosed herein, so long as the requisite hIFN-γ-suppressing activity of the polypeptide is maintained.

Additional residues may also be added at either terminus of a polypeptide for the purpose of providing a "linker" by which the polypeptides of the present invention can be conveniently affixed to a label or solid matrix, or carrier. Amino acid residue linkers are usually at least one residue and may be 40 or more residues, more often 1 to 10 residues. Typical amino acid residues used for linking are tyrosine, cysteine, lysine, glutamic and aspartic acid, or the like. In addition, a peptide may be modified by terminal-NH2 acylation (e.g., acetylation or thioglycolic acid amidation) or by terminal-carboxylamidation (e.g., with ammonia, methylamine, and the like terminal modifications). Terminal modifications are useful, as is well known, to reduce susceptibility by proteinase digestion, and therefore serve to prolong half-life of the peptides in solutions, particularly biological fluids where proteases may be present.

Polypeptides of the invention may comprise naturally occurring amino acids, synthetic amino acids, genetically encoded amino acids, non-genetically encoded amino acids, and combinations thereof. Polypeptides may include both L-form and D-form amino acids.

Representative non-genetically encoded amino acids may include but are not limited to: 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids may include, for example, those molecules in which free amino groups have been derivatized to form amine hydrochlorides, p-toluene sulfonyl groups, carbobenzoxy groups, t-butyloxycarbonyl groups, chloroacetyl groups, or formyl groups. Free carboxyl groups can be derivatized to form salts, methyl and ethyl esters, or other types of esters or hydrazides. Free hydroxyl groups can be derivatized to form O-acyl or O-alkyl derivatives. The imidazole nitrogen of histidine can be derivatized to form N-im-benzylhistidine.

Polypeptides of the present disclosure may be produced using, e.g., recombinant technologies, phage display technologies, synthetic technologies, or combinations of such technologies and other technologies readily known in the art.

Polypeptides of the present invention may be synthesized by any of the techniques that are known to those skilled in the art of peptide synthesis. Synthetic chemistry techniques, such as a solid-phase Merrifield-type synthesis, may be preferred for reasons of purity, antigenic specificity, freedom from undesired side products, ease of production and the like. A summary of representative techniques can be found in Stewart & Young (1969) Solid Phase Peptide Synthesis, Freeman, San Francisco; Merrifield (1969) Adv Enzymol Relat Areas Mol Biol 32:221-296; Fields & Noble (1990) Int J Pept Protein Res 35:161-214; and Bodanszky (1993) Principles of Peptide Synthesis. 2nd rev. ed. Springer-Verlag, Berlin, New York. Solid phase synthesis techniques can be found in Andersson et al. (2000) Biopolymers 55:227-250, references cited therein, and in U.S. Pat. Nos. 6,015,561; 6,015,881; 6,031,071; and 4,244,946. Peptide synthesis in solution is described by Schröder & Lübke (1965) The Peptides, Academic Press, New York. Appropriate protective groups usable in such synthesis are described in the above texts and in McOmie (1973) Protective Groups in Organic Chemistry, Plenum Press, London, New York. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif. and PeptidoGenics of Livermore, Calif.).

Preferably, hIFN-γ polypeptides are produced by nucleic acid recombinant techniques. For instance, hIFN-γ variant polypeptides may be obtained by site directed mutagenesis of a hIFN-γ nucleic acid sequence encoding a wild type IFN-γ polypeptide to introduce nucleic acid changes encoding amino acid modifications of the present disclosure. Resulting nucleic acid sequences encoding hIFN-γ variants may be used to produce the hIFN-γ variants in an expression system using methods known in the art. Additional information may be found in Sambrook et al., Molecular Cloning: A Laboratory Manual (New York: Cold Spring Harbor Laboratory Press, 1989).

All the nucleic acid sequences of the invention may be obtained using a variety of different techniques known in the art. The nucleotide sequences, as well as homologous sequences, may be isolated using standard techniques purchased or obtained from a depository.

Recombinantly-produced hIFN-γ variants may be purified before administration. Methods of purifying proteins are generally known in the art of protein biochemistry. For example, the polypeptides may be purified via standard methods including electrophoretic, molecular, immunological and chromatographic techniques, ion exchange, hydrophobic, affinity, and reverse-phase HPLC chromatography, and chromatofocusing. As another example, the polypeptide may be purified from the flow through of reverse-phase beads. Ultrafiltration and diafiltration techniques, in conjunction with protein concentration, may also be used. For general guidance in suitable purification techniques, see Scopes, R., Protein Purification, Springer-Vertag, N.Y. (1982). Preferably, hIFN-γ variants are purified in two steps by OCTYL-SEPHAROSE® and CM-SEPHAROSE® chromatography as described in the examples and in European Patent Publication No. EP0446582, the disclosure of which is incorporated herein in its entirety.

(b) Compositions

Inactive hIFN-γ variants of the present disclosure may be incorporated into compositions suitable for administration. A composition of the invention may comprise one, or more than one hIFN-γ variant of the disclosure. For instance, a composition of the invention may comprise about 1, 2, 3, 4, 5, 6, 7, 8, 9, or about 10 or more hIFN-γ variants of the disclosure. Preferably, a composition of the disclosure comprises one hIFN-γ variant of the invention.

As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with hIFN-γ variants of the present disclosure, use thereof in the compositions is contemplated. Supplementary active compounds may also be incorporated into the compositions.

A composition of the disclosure may be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes, or multiple dose vials made of glass or plastic.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

Preferably, a composition of the invention is formulated to be compatible with parenteral administration. For instance, compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS).

In all cases, a composition may be sterile and may be fluid to the extent that easy syringeability exists. A composition may be stable under the conditions of manufacture and storage, and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811.

Additional formulations of pharmaceutical compositions may be found in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

One of skill in the art will recognize that the concentration of a hIFN-γ variant of the invention in a composition can and will vary depending in part on the route of administration, the subject, and the reason for the administration, and may be determined experimentally. Methods of experimentally determining the concentration of an active agent, such as hIFN-γ variants of the invention in a composition, are known in the art.

The amount of hIFN-γ variant that may be combined with materials to produce a single dose of an adjuvant composition can and will vary depending upon the hIFN-γ variant, the subject, the formulation, and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711, and from Goodman & Goldman's The Pharmacological Basis of Therapeutics, Tenth Edition (2001), Appendix II, pp. 475-493.

II. Methods

In other aspects, the invention encompasses methods of modulating the biological activity of hIFN-γ. As such, methods of the invention may be used to treat disorders resulting from aberrant activity of hIFN-γ. A method of the invention comprises suppressing the biological activity of hIFN-γ in a subject by administering to the subject a therapeutically effective amount of a composition of the invention comprising a suppressor of hIFN-γ. A suppressor of hIFN-γ and a composition of the invention may be as described in Section I.

(a) Subject

As used herein, the tem "subject" may refer to a living organism having an immune system. In particular, subjects may include, but are not limited to, human subjects or patients and companion animals. Exemplary companion animals may include domesticated mammals (e.g., dogs, cats, horses), mammals with significant commercial value (e.g., dairy cows, beef cattle, pigs, sporting animals), mammals with significant scientific value (e.g., captive or free specimens of endangered species), or mammals which otherwise have value. Suitable subjects may also include: mice, rats, dogs, cats, ungulates such as cattle, swine, sheep, horses, and goats, lagomorphs such as rabbits and hares, other rodents, and primates such as monkeys, chimps, and apes. Preferably, a subject is a human. Subjects may be of any age, including newborn, adolescent, adult, middle age, or elderly.

A suppressor composition of the present disclosure may also be administered in vitro to a cell from a cell line. The cell line may be a primary cell line that is not yet described. Alternatively, a cell line may be an established cell line. A cell line may be adherent or non-adherent, or a cell line may be grown under conditions that encourage adherent, non-adherent or organotypic growth using standard techniques known to individuals skilled in the art. A cell line may be contact inhibited or non-contact inhibited. Preferably, a cell line is an established human cell line. An exemplary cell contacted by a composition of the invention is the amniotic cell line WISH.

(b) Administration

Suppressor IFN-γ variants or compositions comprising suppressor IFN-γ of the present disclosure may also be formulated and administered to a subject by several different means as described in Section I(b). In preferred embodiments, a pharmaceutical composition of the invention is administered by injection.

One of skill in the art will recognize that the amount and concentration of the composition administered to a subject will depend in part on the subject and the reason for the administration. Methods for determining optimal amounts are known in the art. In general, the concentration of a peptide-polynucleotide complex of the invention in a pharmaceutical composition may be as described in Section I(b).

Compositions of the present disclosure are typically administered to a subject in an amount sufficient to provide a benefit to the subject. This amount is defined as a "therapeutically effective amount." A therapeutically effective amount may be determined by the efficacy or potency of the particular composition, the disorder being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining therapeutically effective amounts, one skilled in the art may also consider the existence, nature, and extent of any adverse effects that accompany the administration of a particular compound in a particular subject.

When a composition of the invention is administered to a subject by injection, a composition may be administered to the subject in a bolus. A composition may also be administered by injecting more than one bolus into the subject over a period of time. For instance, a composition may be administered by injecting 1, 2, 3, 4, 5, 6, 7, 8, 9, 10 or more boluses into the subject.

(c) Treating a hIFN-γ-Mediated Disorder

By modulating the biological activity of hIFN-γ, a method of the invention may be used to treat a hIFN-γ-mediated disorder. The term "hIFN-γ-mediated disorder" encompasses any medical condition associated with aberrant function of hIFN-γ. Preferably, a hIFN-γ-mediated disorder is any medical condition associated with increased levels of IFN-γ or increased sensitivity to IFN-γ. As such, a method of the present disclosure may be used to treat an inflammation disorder or an autoimmune disease. For example, the disorder may be Acquired Immune Deficiency Syndrome (AIDS), arthritis, including, but not limited to, rheumatoid arthritis including juvenile rheumatoid arthritis, spondyloarthropathies including ankylosing spondylitis, Sjogren's syndrome, gouty arthritis, osteoarthritis, systemic lupus erythematosus (SLE), lupus nephritis, or juvenile arthritis, Addison's disease, epididymitis, glomerulonephritis, Graves' disease, Guillain-Barre syndrome, Hashimoto's disease, pemphigus, erythropoietin resistance, graft versus host disease, transplant rejection, autoimmune hepatitis-induced hepatic injury, biliary cirrhosis, alcohol-induced liver injury including alcoholic cirrhosis, scleroderma, osteoporosis, vasculitis, alopecia areata, myastenia gravis, and Alzheimer's disease. In some embodiments, the inflammation may be associated with asthma, bronchitis, menstrual cramps, premature labor, tendinitis, bursitis, skin-related conditions such as psoriasis, eczema, psoriatic arthritis, burns and dermatitis, or from post-operative inflammation including from ophthalmic surgery such as cataract surgery and refractive surgery. In a further embodiment, the inflammatory disorder may be a gastrointestinal condition such as inflammatory bowel disease, Crohn's disease, gastritis, irritable bowel syndrome, or ulcerative colitis. In yet another embodiment, the inflammation may be associated with diseases such as vascular diseases, migraine headaches, periarteritis nodosa, thyroiditis, hemolytic anemia, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, allergic rhinitis, respiratory distress syndrome, endotoxin shock syndrome, atherosclerosis, and the like. In an alternate embodiment, the inflammatory disorder may be associated with an ophthalmic disease, such as retinitis, retinopathies, uveitis, ocular photophobia, or of acute injury to the eye tissue. In still another embodiment, the inflammation may be a pulmonary inflammation, such as that associated with viral infections or cystic fibrosis.

Preferably, a method of the invention may be used to treat multiple sclerosis, alopecia areata, myastenia gravis, as well as for graft arteriosclerosis in post-transplanted patients.

Treatment of an IFN-γ-mediated disorder encompasses alleviation of at least one symptom of the disorder, a reduction in the severity of the disorder, or the delay or prevention of progression to a more serious disease that occurs with some frequency following the treated condition. Treatment need not mean that the disorder is totally cured. A useful therapeutic agent needs only to reduce the severity of a disorder, reduce the severity of a symptom or symptoms associated with the disorder or its treatment, or provide improvement to a patient's quality of life, or delay the onset of a more serious disease that can occur with some frequency following the treated condition. For example, if the disorder is graft arteriosclerosis after transplant, a therapeutic agent of the disclosure may prevent graft arteriosclerosis, delay the onset of graft arteriosclerosis, or reduce the luminal stenosis characteristic of graft arteriosclerosis in transplant subjects. When the disorder is alopecia areata, sometimes called spot baldness because it causes bald spots on the scalp, a therapeutic agent of the disclosure may prevent formation of bald spots, may reduce the number of bald spots formed, or may reduce the size of the formed bald spots in a subject.

It will be appreciated by those skilled in the art that a composition of the present disclosure may be used in combination with other therapeutic agents before, after, and/or during treatment with the repressor composition of the disclosure.

DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

The terms "IFN-γ" and "hIFN-γ" refer to the dimeric biologically active form of IFN-γ and hIFN-γ independently of whether this molecule is a wild type or modified form of IFN-γ and hIFN-γ. The terms "IFN-γ polypeptide" and "hIFN-γ polypeptide" refer to a IFN-γ and hIFN-γ monomer.

As used herein, "administering" is used in its broadest sense to mean contacting a subject with a composition of the invention.

As used herein, a "pharmaceutical composition" includes a pharmacologically effective amount of a therapeutic agent of the invention and a pharmaceutically acceptable carrier. As used herein, "pharmacologically effective amount," "therapeutically effective amount" or simply "effective amount" refers to that amount of an agent effective to produce the intended pharmacological, therapeutic or preventive result. For example, if a given clinical treatment is considered effective when there is at least a 15% reduction in a measurable parameter associated with a disease or disorder, a therapeutically effective amount of an agent for the treatment of that disorder or disease is the amount necessary to effect at least a 15% reduction in that parameter.

The term "pharmaceutically acceptable carrier" refers to a carrier for administration of a therapeutic agent. Such carriers may include, but are not limited to, saline, buffered saline, dextrose, water, glycerol, ethanol, and combinations thereof. The term specifically excludes cell culture medium. For drugs administered orally, pharmaceutically acceptable carriers may include, but are not limited to, pharmaceutically acceptable excipients such as inert diluents, disintegrating agents, binding agents, lubricating agents, sweetening agents, flavoring agents, coloring agents and preservatives. Suitable inert diluents may include sodium and calcium carbonate, sodium and calcium phosphate, and lactose, while corn starch and alginic acid are suitable disintegrating agents. Binding agents may include starch and gelatin, while the lubricating agent, if present, may generally be magnesium stearate, stearic acid or talc. If desired, the tablets may be coated with a material such as glyceryl monostearate or glyceryl distearate to delay absorption in the gastrointestinal tract.

The terms "homologous," "identical," or percent "identity" in relation to two or more peptides, refers to two or more sequences or subsequences that have a specified percentage of amino acid residues that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). The definition also includes sequences that have deletions and/or additions, as well as those that have substitutions, as well as naturally occurring, e.g., polymorphic or allelic variants, and man-made variants. As described below, the preferred algorithms can account for gaps and the like.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

Biologically active hIFN-γ is a noncovalent homodimer formed by the self-association of two mature polypeptides in an antiparallel orientation. The mature form of each polypeptide comprises 143 amino acid residues (SEQ ID NO: 5) derived from a precursor form thereof comprising 166 amino acid residues. Numbering of amino acids is from the N-terminus of hIFN-γ of SEQ ID NO: 5.

In practicing the present invention, many conventional techniques in molecular biology, microbiology, and recombinant DNA may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization 1985, (Hames and Higgins eds.); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian cells, 1987 (J. H. Miller and M. P. Calos eds., Cold Spring Harbor Laboratory); and Methods in Enzymology, Vol. 154 and Vol. 155 (Wu and Grossman, and Wu, eds., respectively).

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of hIFN-γ Derivative Proteins with Amino Acid Substitutions at Positions 86, 87 and 88

Recombinant proteins derivative of the hIFN-γ with amino acid substitutions at positions 86, 87 and 88 were prepared by PCR mutagenesis of a synthetic hIFN-γ gene using appropriate primers. The latter were synthesized on a Cyclone Plus (MilliGen/Biosearch) synthesizer using the phosphoramidite method and purified on a 15% polyacrylamide gel. Two primers (forward and reverse) were synthesized and their primary structure is presented in the sequence listing. The forward primer (SEQ ID NO: 1) was designed to introduce a HindIII site and the reverse primer (SEQ ID NO: 2) contains a randomized 9 nucleotide long region plus an AsuII site. The HindIII and AsuII restriction sites were used for cloning PCR fragments into the pJP1R3-hIFN-γ expression vector as described in the International Patent Publication No. WO2006099701, the disclosure of which is incorporated herein in its entirety. A synthetic hIFN-γ nucleic acid sequence encoding wild type hIFN-γ of SEQ ID NO: 5 was used as a template. The PCR conditions used are presented in Tables 2 and 5.

TABLE 2

PCR conditions for primers SEQ ID NO: 1 and SEQ ID NO: 2

| Program | Number of cycles | Time (min) | Temperature (° C.) |
|---|---|---|---|
| I | 1 | 5 | 94 |
| II | 5 | 0.5 | 94 |
|  |  | 0.5 | 38 |
|  |  | 0.5 | 74 |
| III | 35 | 0.5 | 94 |
|  |  | 0.5 | 55 |
|  |  | 0.5 | 74 |
| IV | 1 | 10 | 74 |

The PCR fragments were purified by electrophoresis in 1.5% Agarose Type II gel (Sigma), digested with HindIII and AsuII, and cloned into the pJP1R3-hIFN-γ expression vector that was pre-digested with HindIII and AsuII as described in International Publication No. WO2006099701. To this end 20 μg plasmid (vector) DNA was dissolved in 150 μl HindIII buffer and digested with 20 U HindIII for 3 h at 37° C. The reaction mixture was treated consecutively with phenol and chloroform and DNA was precipitated with 3 v/v of ethanol at −20° C. The precipitate was dissolved in 150 μl AsuII buffer and digested with 20 U AsuII for 3 h at 37° C. The linear vector was dephosphorylated with calf intestinal alkaline phosphatase (CIAP, Boehringer Mannhein), purified using agarose gel electrophoresis, and mixed in T4 DNA ligase buffer with the PCR fragments at a ratio 3:1. The ligase reaction was carried out overnight at 4° C., and used for transformation of competent E. coli LE392 cells.

The transformed cells were grown in standard Luria-Bertani (LB) broth and/or LB-agar containing 50 μg/ml ampicillin and 10 μg/ml tetracycline. A set of 162 clones were selected, plasmid DNA was isolated from each clone, and the exact nucleotide sequence of the randomized region was determined by DNA sequence analysis. Thus, the number of individual clones was reduced to 101 (Table 1), all of which were tested for production of hIFN-γ derivative proteins. The level of expression of the latter was determined by ELISA using hIFN-γ specific monoclonal antibodies.

The hIFN-γ derivative proteins were purified in two steps using OCTYL-SEPHAROSE® and CM-SEPHAROSE® (Pharmacia) chromatography as previously described in European Patent Application No. EP0446582, the disclosure of which is incorporated herein in its entirety.

Two biological activities, antiviral and antiproliferative, were determined for the hIFN-γ derivative proteins. The antiviral activity (expressed in International Units) was measured by the protective effect of hIFN-γ against the cytopathic action of vesicular stomatitis virus (VSV) on the amniotic cell line WISH [12], and the antiproliferative activity was determined using the kynurenine bioassay [13]. Table 3 presents activity data of some of the mutant hIFN-γ proteins. Both activities vary between $4.3 \times 10^4$ and $1.2 \times 10^4$ IU/mg for constructs 19 and 46-1, respectively. This is much lower in comparison with the activity of intact hIFN-γ ($10^7$-$10^8$ IU/mg). No biological activity was registered for the constructs 27, 36, 134, 135 and 144.

TABLE 3

| Construct No | hIFNg: Amino acids at positions 86, 87, 88 | | | Specific Biological Activity (IU/mg) measured in cell lysates |
|---|---|---|---|---|
| 19 | Ser | Thr | Phe | $2 \times 10^4$ |
| 22 | Ser | Ser | Leu | $3 \times 10^5$ |
| 27 (SEQ ID NO: 6) | Glu | Met | Pro | No |
| 28 | Leu | Thr | Pro | No |
| 36 | Leu | Cys | Pro | No |
| 39-12 | Asp | Leu | Leu | No |
| 46-1 | Thr | Leu | Leu | $4.9 \times 10^6$ |
| 63 | Arg | Leu | Arg | No |
| 72 | His | Ser | Arg | No |
| 74 | Ser | Leu | Leu | $2.4 \times 10^7$ |
| 85 | Arg | Arg | Ser | No |
| 105-2 | Ala | Thr | Ala | No |
| 115 | Gln | Phe | His | No |
| 120 | Gln | Ala | Gly | No |
| 134 (SEQ ID NO: 7) | Thr | Asn | Gly | No |
| 135 | Val | Ser | Pro | No |
| 143 | Cys | Ser | Pro | No |
| 144 | Cys | Ala | Pro | No |

Example 2

Construction of hIFN-γ Derivative Protein with Gln at Position 88

A recombinant protein derivative of hIFN-γ comprising Gln instead of Lys at position 88 (Gln/Lys88) was prepared by PCR mutagenesis using a synthetic hIFN-γ gene as a template and the primers having the nucleic acid sequences of SEQ ID NO: 1 and SEQ ID NO: 3. The forward primer (SEQ ID NO: 1) is as described in Example 1 above, and the reverse primer (SEQ ID NO: 3) comprises a single nucleotide transition (A→G) to substitute Gln for Lys at position 88. It also carries an AsuII site for cloning into the expression vector pJP1R3-hIFN-γ. PCR conditions are presented in Tables 4 and 5 and all subsequent procedures were performed as described in Example 1.

TABLE 4

PCR conditions for primers SEQ ID NO: 1 (forward) and the reverse primers SEQ ID NO: 3 or SEQ ID NO: 4

| Program | Number of cycles | Time (min) | Temperature (° C.) |
|---|---|---|---|
| I | 1 | 5 | 94 |
| II | 5 | 1 | 94 |
|  |  | 1 | 50 |
|  |  | 1 | 74 |

TABLE 4-continued

PCR conditions for primers SEQ ID NO: 1 (forward) and
the reverse primers SEQ ID NO: 3 or SEQ ID NO: 4

| Program | Number of cycles | Time (min) | Temperature (° C.) |
|---|---|---|---|
| III | 35 | 1 | 94 |
|  |  | 1 | 65 |
|  |  | 1 | 74 |
| IV | 1 | 10 | 74 |

TABLE 5

Composition of PCR reaction mixture

| Ingredients | Quantity (μl) |
|---|---|
| Template DNA (50 pg/μl) | 1 |
| Forward primer (20 pmol/μl) | 1 |
| Reverse primer (20 pmol/μl) | 1 |
| Taq-polymerase (3 U/μl) | 1 |
| 10 × PCR buffer | 2 |
| 2 mM dNTP's | 2 |
| H$_2$O | 12 |
| Total | 20 |

The resulting Gln/Lys88 derivative hIFN-γ demonstrated almost 1000 fold lower antiviral and antiproliferative activities in comparison with the wild type hIFN-γ (Table 6).

Example 3

Construction of a hIFN-γ Derivative Protein with Gln at Position 88 and Deleted 21 C-Terminal Amino Acids A recombinant protein derivative of the hIFN-γ containing both a Lys88→Gln substitution and deletion of 21 C-terminal aminoacids (Lys/Gln88/T7) was prepared by PCR mutagenesis using the hIFN-γ derivative described in Example 2, and the primers SEQ ID NO: 1 and SEQ ID NO: 4. The forward primer (SEQ ID NO: 1) is as described in Example 1, and the reverse primer (SEQ ID NO: 4) was designed to eliminate 21 3'-terminal codons from the hIFN-γ gene during PCR amplification. The resulting PCR product is a nucleic acid sequence coding for 122 amino acids and a substitution of Gln for Lys at position 88. It carries two restriction sites (HindIII and BamHI) for cloning into the expression vector pJP1R3-hIFN-γ also digested with HindIII and BamHI. The PCR reaction conditions are presented in Tables 4 and 5. All subsequent procedures were performed as in Example 1.

As it is seen in Table 6, the Gln/Lys88/T7 mutant demonstrates more than 1000 fold decrease in both antiviral and antiproliferative activities in comparison to the wild type hIFN-γ.

TABLE 6

| Construct No | hIFNg: Amino acids at positions 86, 87, 88 | Specific Biological Activity (IU/mg) measured in cell lysates |
|---|---|---|
| LG88 (SEQ ID NO: 9) | Lys Lys Gln | $1.7 \times 10^5$ |
| Lys/Gln88/T7 | Lys Lys Gln + truncated C-terminus | $6.7 \times 10^3$ |

TABLE 6-continued

| Construct No | hIFNg: Amino acids at positions 86, 87, 88 | Specific Biological Activity (IU/mg) measured in cell lysates |
|---|---|---|
| T8 | Lys Lys Lys + Truncated 24 C-terminal aa | No |
| T9 | Lys Lys Lys + Truncated 27 C-terminal aa | No |

Example 4

Examination of the Suppressor Activity of Mutant hIFN-γ Proteins

The ability of mutant hIFN-γ derivative proteins described in the previous examples to compete with the wild-type hIFN-γ for the hIFN-γ receptor was examined using the amniotic cell line WISH (enriched in hIFN-γ receptors). The competition assay measured the decrease in antiproliferative activity of standard (wild-type) hIFN-γ in the presence of mutant hIFN-γ derivative proteins. The antiproliferative activity was determined using the kynurenine bioassay [13] based on the hIFN-γ induction of indoleamine-2,3-dioxygenase (IDO), which is the first and rate-limiting enzyme in the tryptophan catabolism. IDO catalyzes oxidative cleavage of tryptophan, to N-formylkynurenine. Following a hydrolysis step, N-formylkynurenine is transformed into kynurenine which gives a yellow-colored compound when contacted with Ehrlich's reagent. The level of the yellow-colored compound may be measured at 490 nm. It is known that the amount of produced kynurenine is directly proportional to the concentration of hIFN-γ used for cell activation.

To measure the suppressor activity, mutant proteins were mixed in equimolar amounts in sterile bacterial lysates with purified hIFN-γ, and the antiproliferative activity of the mixtures was determined by the kynurenine bioassay using wild-type hIFN-γ as a standard. Experimentally, clear cell lysates of *E. coli* LE392 cells transformed with plasmids expressing mutant hIFN-γ proteins were prepared after cultivation in LB broth supplemented with 50 μg/ml ampicillin to a cell density of $A_{590}$=0.7. Samples of 2 $OD_{590}$ cells were centrifuged, the cells were resuspended in 1 ml 0.14 M NaCl, 10 mM Tris pH 8.0, 0.1 mM PMSF and disrupted by sonication. The lysates were cleared by centrifugation at 12000 rpm for 15 min at 4° C., and used for further analyses.

Total protein content was determined using the Bradford assay with bovine serum albumin (fraction V) as a standard. The samples were diluted by PBS (14.7 mM $Na_2CO_3$, 34 mM $NaHCO_3$, pH 9.6) to a final concentration of 27 μg/ml protein. Samples of 50 μl were added (11 times per sample) to PVC 96 well microplates (Costar Ltd., USA), incubated overnight at 4° C., and the content of hIFN-γ or hIFN-γ derivative proteins was measured by ELISA using hIFN-γ specific monoclonal antibodies.

To measure the suppressive effect of the hIFN-γ mutant proteins against binding of wild-type hIFN-γ to the cell receptors, clear cell lysates were serially diluted, and samples of 50 μl were mixed with 50 μl of standard hIFN-γ and added to PVC 96 well microplates. WISH cell suspension (50 μl) in MEM Eagle medium supplemented with HEPES, L-glutamine and 2% BFS was added, mixed with 50 μl L-tryptophan and the kynurenine bioassay was performed as described [13]. The final concentration of the standard hIFN-γ in the analyzed samples was 25 IU/ml, 50 IU/ml and 100 IU/ml, corresponding to 0.027 nmol, 0.055 nmol and 0.11 nmol, respectively. Samples containing standard hIFN-γ (alone) were used as positive control, and clear cell lysates obtained from host (non-transformed *E. coli* LE392) cells were used as negative controls in this assay.

The results can be interpreted as follows: if a mutant protein has the same affinity to the hIFN-γ receptor as that of the wild type hIFN-γ and zero antiproliferative activity, the activity of the equimolar mixture of both substances should be 50% of that of the control (pure wild type hIFN-γ). The data presented in Table 7 show that the constructs with zero antiproliferative activity (constructs 27 and 134), and also the C-terminally truncated construct Lys/Gln88/T7, demonstrate strongest suppressive effect.

TABLE 6

Mutant hIFN-γ gene variants

| Clone signature | Nucleotide sequence between nucleotides 218 and 227 | Amino acids at positions 86, 87 and 88 | Specific activity of the mutant hIFN-γ proteins (IU/mg) | Competition with the wild type hIFN-γ |
|---|---|---|---|---|
| 19 | TCC ACT TTT | Ser Thr Phe | *$7.2 \times 10^5$<br>**$2 \times 10^4$ | + |
| 27 | GAA ATG CCC | Glu Met Pro | 0 | +++ |
| 36 | CTG TGT CCC | Leu Cys Pro | 0 | ++ |
| 46-1 | ACC CTC CTC | Thr Leu Leu | *$3.0 \times 10^4$ | + |
| 134 | ACC AAT GGT | Thr Asn Gly | 0 | +++ |
| 135 | GTT TCC CCC | Val Ser Pro | 0 | + |
| 144 | TGC GCC CCT | Cys Ala Pro | 0 | + |
| Lys/Gln88 | CCG TAC CTC | Lys Lys Gln | *$1.7 \times 10^5$<br>**$1.2 \times 10^4$ | + |
| Lys/Gln88/T7 | CCC AAT TAT | Lys Lys Gln and C-terminus deleted | *$6.7 \times 10^3$<br>**$4.3 \times 10^4$ | +++ |

*antiproliferative activity;
**antiviral activity;
"+" Competition with the wild type hIFN-y,
"+++" high competition,
"+++" intermediate competition,
"+" low competition The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

REFERENCES

1. Johnson, K. P. (1988) Treatment of multiple sclerosis with various interferons. The Cons. Neurology, 38 (suppl. 2) 52-64.
2. Martino, G., Moiola, L., Brambilla, E., Clementi, E., Comi, G., Grimaldi, L. M. (1995). Interferon gamma induces T lymphocyte proliferation in multiple sclerosis via a Ca2+-dependent mechanism. J. Neuroimmunol. 62, 169-176.
3. Vartanian, V., Li, Y., Zhao, M., Stefansson, K. (1995) Interferon-gamma-induced oligodendrocyte cell death: implications for the pathogenesis of multiple sclerosis. Mol. Med. 1, 732-743.
4. Tellides, G., Pober, J. (2007) Interferon-γ axis in graft arteriosclerosis. Circ. Res. 100, 622-632.
5. Panitch, H. L., Hirsch, R. L., Schindler, J., Johnson, K. P. (1987) Treatment of multiple sclerosis with gamma interferon: Exacerbations associated with activation of the immune system. Neurology 37, 1097-1102.
6. Beck, J., Rondot, P., Catinot, L., Falcoff, E., Kirchner, H., Wietzerbin, J. (1988) Increased production of interferon gamma and tumor necrosis factor precedes clinical manifestation in multiple sclerosis: do cytokines trigger off exacerbations? Acta Neurol. Scand. 78, 318-323.
7. Furlan, R., Bergamim A., Lang, R., Brambilla, E., Franciotta, D., Martinelli, V., Comi, G., Paninam P., Martino. G. (2000) Interferon-beta treatment in multiple sclerosis patients decreases the number of circulating T cells producing interferon-gamma and interleukin-4. J. Neuroimmunol. 111, 86-92.
8. Khademi, M., Wallstrom, E., Andersson, M., Piehl, F., Di Marco, R., Olsson, T. (2000) Reduction of both pro and anti-inflammatory cytokines after 6 months of interferon beta-1a treatment of multiple sclerosis. J. Neuroimmunol. 103, 202-210.
9. Skurkovich, S., Boiko, A., Beliaeva, I., Buglak, A., Alekseeva, T., Smirnova, N., Kulakova, O., Tchechonin, V., Gurova, O., Deomina, T., Favorova, O. O., Skurkovic, B., Gusev, E. (2001) Randomized study of antibodies to IFN-gamma and TNF-alpha in secondary progressive multiple sclerosis. Mult. Scler. 7, 277-284.

10. Skurkovich, B., Skurkovich, S. (2003) Anti-interferon-gamma antibodies in the treatment of autoimmune diseases. Curr. Opin. Mol. Ther. 5, 52-57.
11. Espejo, C., Penkowa, M., Satz-Torres, I., Xaus, J., Celada, A., Montalban, X., Martinez-Caceres, E. M. (2001) Treatment with anti-interferon-gamma monoclonal antibodies modifies experimental autoimmune encephalomyelitis in interferon-gamma receptor knockout mice. Exp. Neurol. 172, 460-468.
12. Forti, R. L., Schuffman, S. S., Davies, H. A. and Mitchell, W. M. (1986) Objective antiviral assay of the interferons by computer assisted data collection and analysis. Methods in Enzymol. 119, 533-540.
13. Boyanova, M., Tsanev, R. and Ivanov, I. (2002) A modified kynurenine bioassay for quantitative determination of human interferon gamma. Analyt. Biochem. 308, 178-181.

What is claimed is:

1. A composition comprising an IFN-γ suppressor, wherein the IFN-γ suppressor has preserved affinity to an IFN-γ receptor, and wherein the IFN-γ suppressor has the amino acid sequence of SEQ ID NO: 5, wherein positions 86, 87 and 88 have been substituted with:

His Val Cys (Construct No. 6),
Thr Phe Trp (Construct No. 12),
Leu Pro Phe (Construct No. 14),
Ser Thr Phe (Construct No. 19),
Ser Ser Leu (Construct No. 22),
Ser Val Ser (Construct No. 26),
Glu Met Pro (Construct No. 27),
Leu Cys Pro (Construct No. 36),
Thr Leu Leu (Construct No. 46-1),
His Pro Leu (Construct No. 61),
Phe Thr Arg (Construct No. 62),
Arg Leu Arg (Construct No. 63),
Ser Phe Phe (Construct No. 97),
Phe Leu Val (Construct No. 108),
Ser Leu Phe (Construct No. 123),
Pro Pro Ser (Construct No. 133),
Thr Asn Gly (Construct No. 134),
Val Ser Pro (Construct No. 135),
Cys Ala Pro (Construct No. 144), or
Lys Lys Gln (Construct Lys/Gln88), or the IFN-γ suppressor has the amino acid sequence of SEQ ID NO:5 with positions 86-88 substituted with Lys Lys Gln and wherein the C-terminus is deleted (construct Lys/Gln88/T7).

2. The composition of claim 1, wherein the IFN-γ suppressor is deficient in inducing signal transduction.

3. The composition of claim 1, wherein the IFN-γ suppressor is capable of suppressing bioactivity of endogenous IFN-γ.

4. The composition of claim 1, wherein the modification of the amino acid sequence of the IFN-γ suppressor is introduced by using a forward primer having a sequence consisting of SEQ ID NO: 1 and a reverser primer having a sequence selected from the group consisting of SEQ ID NO: 2, SEQ ID NO: 3, and SEQ ID NO: 4.

5. A method of inhibiting the biological activity of endogenous IFN-γ, the method comprising:
a. identifying a subject in need of IFN-γ inhibition;
b. contacting the subject with a therapeutically effective amount of the composition of claim 1; and,
c. suppressing the biological activity of endogenous IFN-γ in the subject.

6. The composition of claim 1, wherein the IFN-γ suppressor is a dimer of IFN-γ polypeptides, and comprises at least one modified IFN-γ polypeptide.

7. The composition of claim 6, wherein the IFN-γ suppressor is a dimer of IFN-γ polypeptides, and comprises one modified IFN-γ polypeptide and one wild type IFN-γ polypeptide.

8. The composition of claim 6, wherein the IFN-γ suppressor is a dimer of IFN-γ polypeptides, and comprises two modified IFN-γ polypeptides.

9. The composition of claim 8, wherein each of the two IFN-γ polypeptides comprises the same modification.

10. The composition of claim 8, wherein each of the two IFN-γ polypeptides comprises a different modification.

* * * * *